United States Patent [19]

Farges

[11] 4,045,125
[45] Aug. 30, 1977

[54] BAND FILTERS FOR USE IN PROTECTIVE GLASSES

[75] Inventor: Guy Farges, Paris, France

[73] Assignee: Etat Francias, Paris, France

[21] Appl. No.: 589,511

[22] Filed: June 23, 1975

[30] Foreign Application Priority Data

June 27, 1974 France ............................ 74.22356

[51] Int. Cl.² .............................................. G02B 5/28
[52] U.S. Cl. ..................................... 350/166; 351/44; 427/166
[58] Field of Search ............................. 350/163–166, 350/314, 2; 427/166, 250, 255; 351/44

[56] References Cited

U.S. PATENT DOCUMENTS

| 2,758,510 | 8/1956 | Auwater | 350/166 |
| 3,649,359 | 3/1972 | Apfel et al. | 350/166 |
| Re. 27,473 | 9/1972 | Mauer | 350/165 |

*Primary Examiner*—Jon W. Henry

[57] ABSTRACT

A band filter adapted to pass only a band of determined wave length of the electromagnetic spectrum and comprising a support, at least partially transparent in the considered band, covered on one of its surfaces by a filtering element constituted of three metallic layers separated respectively by two layers of transparent material. The filter can employ anti-reflection coatings and binding and adherency layers.

12 Claims, 6 Drawing Figures

BAND FILTERS FOR USE IN PROTECTIVE GLASSES

FIELD OF THE INVENTION

The present invention relates to band filters adapted to isolate a portion of the electromagnetic spectrum whatever its position in the spectrum. It is concerned particularly with filters whose band length is between 400 and 700 nm, adapted notably to protect a viewer's eyes against ultraviolet and infrared radiation of the electromagnetic spectrum.

BACKGROUND AND PRIOR ART

It is well known that the phenomena of vision is assured by radiation solely in the visible spectrum, that is to say, electromagnetic radiation having a wave length between about 400 and 700 nm. This radiation is not dangerous to the eye if its intensity is not too great, in contrast with ultraviolet and infrared radiation which can produce severe lesions even at a relatively weak dosage. The ideal protection filter for the eye should therefore have a maximum factor of transmission in the domain of greatest sensitivity of the eye to attenuate the visible light in order to avoid brightness or glare in an intense luminous flux and to totally eliminate ultraviolet and infrared radiation by absorption or reflection.

The protection of the eyes against objectionable radiation in the electromagnetic spectrum is most often obtained by the use of semitransparent mineral or organic glass generally referred to as "sunglasses". The partial transmission in the visable light region is generally obtained by introducing a colorant into the body of the glass or plastic material. Certain compositions permit achieving a good protection of the eyes but necessitate a coating of special expensive materials. The lenses of sunglasses widely distributed in the market do not generally contain such materials and lead to very poor protection since they reduce the visible radiation but allow passage of a substantial portion of the ultraviolet and infrared radiation. The eye compensates for the reduction of the visible light by a greater opening of the iris and, under these conditions, receives a much greater amount of harmful energy than in the absence of any protection.

In addition to the great variety of tinted mineral and organic glasses, other solutions have been proposed for the protection of the eyes and notably the utilization of filters comprising a support of glass or plastic material covered with one or a plurality of thin metallic layers particularly of gold or copper. U.S. Pat. Nos. 3,118,781; 1,222,049; 2,087,802; and 2,854,349 concern such filters. Nevertheless, these filters which give satisfactory results in a great number of utilizations, for example, the protection of the eyes of welders, cannot be employed generally and cannot be applied to sunglasses, in particular because the internal surface of this type of filter is very reflective and the eye receives, without filtering, the greatest portion of the light arriving at the rear and reflected by the filter.

Another known solution consists of utilizing mixed filters composed of a support covered with a metallic layer isolated by two transparent layers. In addition to the problems posed by the practical realization of such filters, in particular the control of the thickness of the layers, the obtained spectrum is still remote from that of the ideal filter.

This type of filter has been perfected, particularly for the purpose of manufacturing of sunglasses, as shown in French Pat. No. 2003177 by covering the internal face of the filter with a metallic layer of much smaller thickness than the metallic filtering layer which serves as an anti-reflection layer which eliminates in part the reflection of light at the rear face of the filter. However, this filter retains the disadvantage of layers having metallic filters which considerably attenuate the visible range without providing sufficient protection in the ultraviolet and infrared ranges while additionally it does not assure sufficient protection in the case of intense ultraviolet and infrared emission.

FIG. 1 of the attached drawings allow a comparison of the transmission curves as a function of the wave length of an ideal filter (curve 1), conventional sunglasses (curve 2), and a mixed filter such as that described in French patent 2000177 (curve 3). As can be readily seen, none of the tested filters assures protection in the infrared region and in the mixed filter described in the French patent, the percentage of visible light which is transmitted is very low.

SUMMARY OF THE INVENTION

An object of the present invention is to provide a band filter in the visible range having characteristics approaching, as closely as possible, that of the ideal filter such as is represented by curve 1 in FIG. 1. The present invention also contemplates a band filter more generally which permits the isolation of any portion whatever of the electromagnetic spectrum. In order to achieve this, the present invention proposes a band filter adapted to pass only a band of determined wave length of the electromagnetic spectrum comprising a support at least partially transparent in the considered band, covered on at least one of its faces by a filter element constituted of three metallic layers respectively separated by two transparent layers. More particularly, the present invention contemplates a band filter in the visible region whose wave length is situated between 350 and 750 nm which comprises a support at least partially transparent in the considered band, covered on at least one of its faces by a filtering element constituted of three metallic layers respectively separated by two transparent layers whose index of refraction is greater than 1.5. The optical thickness, i.e. the product of the actual thickness by the index of refraction of the transparent layers is preferably equal to about ¼ of the mean wave length of the considered band.

The metallic layers of the band filters according to the present invention can be made from any one of the metals ordinarily employed in interference filters such as, in particular, aluminum, silver, rhodium, and platinum, but there is advantageously employed copper or gold.

Furthermore, the transparent layers utilizable in the band filters according to the present invention, can be selected from transparent material currently utilized in interferential optics and for the fabrication of sunglasses, i.e., in particular, dielectric materials such as bismuth oxide, lead oxide, tin oxide, indium oxide, titanium dioxide, zirconium oxide, niobium oxide, tantulum pentoxide, aluminum oxides, silicon oxides and zinc sulfide. In general manner, all transparent material whose index of refraction is greater than 1.5 can be utilized to form the transparent layers of the band filters in the visible region according to the present invention. Nevertheless, there is advantageously utilized materials having very high indexes of refraction, such as titanium dioxide and zinc sulfide. The utilization of such materials improves the effect of transparency of the filter in the visible range, and increases the density in the ultraviolet and infrared ranges. In other words, for a given metal, for example, gold or copper, the contrast factor of the optical filtering element in the visible range will be increased as the index of refraction of the transparent material is increased.

The value of the maximum transmission factor and the shape of the visible spectrum depends greatly on the thickness of the metallic layers. These should therefore be measured with great precision. The thickness and the index of refraction of the transparent layers determines the width of the band of the filter and its position in the electromagnetic spectrum.

It is obvious that if the transparent layer has an index of refraction lower than that of zinc sulfide, it will be necessary to utilize a much greater thickness in order to remain in the vicinity of the condition designated previously, viz. the optical thickness in the region of $\lambda_m/4$ ($\lambda_m$ = the mean wave length of the considered band).

The transparent or partially transparent support utilizable in the band filter according to the present invention, can be made of any material having the characteristics of necessary transparency while having good mechanical resistance. Thus, for the band filter in the visible range, this support can be, for example, glass or any plastic material. It can be entirely transparent, partially colored or have received a preliminary treatment which can be of any nature whatsoever.

For a judicious choice of the optical constants of the transparent layers and of the metallic layers, it is possible to reduce the undesirable optical effects at the different interfaces of the metallic and dielectric layers and to obtain a maximum transparency in the visible range. The curve of the spectral response of the optical filtering element generally presents a more or less pronounced hollow at the center of the spectrum or a slight asymmetry. However, if the thickness and the indices of refraction of the metallic and dielectric layers are suitably chosen, the spectral response of the optical filtering element can be substantially constant at about 100 nm. This result is easily obtained, for example, in the visible range with the combination of gold and zinc sulfide, when the thicknesses of the three metallic layers are equal and between 40 and 60 nm, the thickness of the transparent layers being between 50 and 70 nm, the thickness of the transparent layers in fact not being critical. The variation should nevertheless be situated in a reasonable limit of the order of 10%. Such imprecision sensitively displaces the wave length from the center of the spectrum and diminishes the transparency in the visible region, but does not notably affect the spectral response of the filtering element.

In the preferred embodiment of the band filter in the visible range according to the invention, the filtering element is completed by an anti-reflection coating adapted to reduce the reflection from the light falling on the rear face of the filter, this coating comprising a metallic or semi-metallic layer of the anti-reflection coating.

The materials which can be utilized for the anti-reflection metallic layer will be preferably selected from iron, titanium, tungsten, nickel, tantulum, molybdenum, niobium, zinc, cadmium, vanadium, chromium, tin, indium, lanthanum, lead, aluminum zirconium, iridium yttrium, hafnium, rhenium, cobalt, thallium and platinum. It is possible to utilize as well semi-metallic elements such as germanium, silicon, antimony, tellurium and arsenic. These semi-metallic materials, in particular germanium, can also be utilized in the manufacture of the transparent layer of the filtering element if a band filter in the infrared range is to be obtained. Nevertheless, for the anti-reflection coating it is particularly advantageous to employ neutral optical materials such as certain alloys e.g. Inconel or other alloys of nickel and chromium.

The transparent layer of the anti-reflection coating is constituted by a layer of material as cited above for the constitution of the filtering element. It is to be noted that as for the filtering element, the anti-reflection coating will be more efficient as the index of refraction of the transparent layers is increased.

When the selected embodiment is such that the optical filtering element is interposed between the support and the eye, the metallic or semi-metallic layer of the anti-reflection coating will be applied on the last metallic layer of the filtering element, and then there will be placed the transparent layer of the anti-reflection coating. If the inverse embodiment is chosen, the transparent layer will be contiguous with the support and then there will be disposed thereon the metallic layer and then the optical filtering element. The transparency of the optical element can be increased further by applying an anti-reflection coating on opposite sides thereof.

The essential function of the metallic layer is to absorb the light arriving at the rear face of the filter before it falls on the first metallic layer of the optical filtering element. However, it must have a partial transmission sufficient to allow passage of the light arriving on the eye in the normal direction after having traversed the filtering element. The light arriving in the other direction from the rear face, in the case of sunglasses, is lowered a first time by traversing the metallic layer of the anti-reflection coating, a portion of the residual light traversing the filtering element while the other portion is reflected on itself to be sent towards the eye after having traversed anew the metallic layer which will attenuate it still further. The light arriving in the direct direction only traverses the metallic layer once, whereas that falling on the rear face traverses this layer two times and is thereby sufficiently reduced so as to be without danger to the eye even if the metallic layer is of notable transparency.

The transparent layer of the anti-reflection coating of high refraction index has for its principal purpose the elimination of reflection introduced at the preceding metallic layer. The metallic layer of the anti-reflection coating after application of the transparent layer acts therefore principally as an absorbent layer. It is preferred that this have a relatively low thickness and present a neutral spectrum of absorption in order that its application does not substantially modify the spectral response of the filtering element. The anti-reflection coating will have a metallic layer of a thickness preferably between 5 and 20 nm. The thickness of the corresponding transparent layer will be preferably between 35 to 45 nm. If the thickness and the optical constants of the metallic layer and of the transparent layer are adapted, the residual reflection can be very low and the transparency of the optical filtering element increased by this treatment, particularly in the region of short wave lengths.

The filtering element can, in general, be disposed directly on the support whatever the nature of the latter. However when certain metallic layers are utilized, notably, gold, it may be necessary to obtain a good adherance and for this purpose there is interposed between the support and the first metallic layer of the filtering element a bonding layer. The nature of this will be selected as a function of the nature of the support and generally they can be the same as the elements or alloys utilizable for the metallic or semi-metallic layers of the anti-reflection coating. Details on this subject can be found in the work of L. Holland "Vacuum Deposition of Thin Films". When the metallic constituent of the optical filtering element is gold, it is preferred to utilize as the binding layer, on supports of glass or plastic material, an oxidizable material such as chromium or the alloys of nickel and chromium. Layers satisfying the tests of adherency such as defined by standards will be obtained with thicknesses preferably between 10 and 15 nm. If this thickness is observed, the spectral response of the optical filtering element is not substantially affected.

The adherence of the transparent dielectric layers to the metallic layers is generally sufficient to meet the tests for adherency. In contrast, with certain combinations of dielectrics and metals there is found a deficiency of adherence between the metal and the dielectric. This phenomena is observed, for example, with the combination of gold and zinc sulfide when these materials are deposited under certain conditions on supports of plastic material. This can be corrected by selecting and interposing between each transparent layer and the adjacent metallic layer of the filtering element an adherence layer of the same nature as the aforedescribed binding layer. When the thickness of the intermediary adherence layer is between about 5 and 7 nm, the optical filtering element will satisfy the tests of adherency, and its transparency in the visible range is not notably diminished, while the width of the passing band is improved.

The band filters according to the invention composed of a plurality of thin metallic or semi-metallic layers and intermediate transparent layers are stable under the normal conditions and atmospheres of utilization. However, their resistance to abrasion which depends on the utilized material is often low. Even if they can be subjected to a number of cleaning steps without deterioration, it is preferred to protect them by a thick layer of a material resistant to abrasion and to the action of certain corrosive agents. The protective layer can be a polymeric material such as polyethylene, polypropylene, polyterephthalate, ethylene glycol or any other plastic material which is sufficiently resistant to abrasion. It can also be constituted by silica, magnesium fluoride, chromium oxide, or glass. In a general manner, there can be utilized any transparent material having good resistance to abrasion and to the action of active chemicals.

According to the selected embodiment, the protective layer is either the first or the last layer which the light meets in the course of its travel through the composite filter.

The metallic layers and the transparent layers of the filtering element according to their nature and that of the support can be deposited by different techniques such as electrolysis, chemical vapor phase processes, cathodic pulverization, thermal evaporation under vacuum or by any of the techniques utilized for the deposit of thin layers. Among all of these techniques, vacuum deposition is particularly advantageous for the present invention. This process permits deposition of a variety of metallic, dielectric or semi-metallic layers on any type of support. It gives the most uniform and optically perfect layers. It offers the possibility of evaluating with great precision the thickness of the different layers during their deposit and of treating a substantial number of supports simultaneously. The specialized literature has been devoted to a number of articles on this subject. The work of L. Holland "Vacuum Deposition of Thin Films" contains a number of teachings such as regards the technique for realization of properties of the layers as a function of the parameters of deposit for most of the materials utilizable in the present invention, notably those which are preferred i.e. gold, copper and zinc sulfide. The layers of gold or of copper can be obtained by vacuum deposition of the metals in a container of heated tungsten by Joule effect at a temperature between 1200° and 1400° C. By the same technique, layers of zinc sulfide can be obtained by heating the material in a molybdenum or tantulum container at a temperature between 1100° and 1300° C. To obtain hard layers which are substantially insoluble in water and basic solutions, it is preferred to utilize a very pure material and to heat the support to 300° C. If this temperature is not compatible with the nature of the support, for example, plastic materials, the resistance of layers of zinc sulfide will be improved by a prolonged heating at a temperature of about 80° C.

With regard to the application of the protection layer, this should not lead to deformation of the support. It can be realized by diverse treatments such as vapor phase deposit, tempering, rolling, thermal evaporation under vacuum, cathodic pulverization, etc. U.S. Pat. No. 3,322,565 describes a process for deposit of a polymer which utilizes heating by electronic bombardment. This technique is also preferred for the deposit of silica or of glass, e.g. type 8329, sold by the Societe Schott.

If necessary, there can be interposed between the filter and the protection layer a binding layer as described previously of a thickness between about 4 and 7 nm.

In order to illustrate certain embodiments of the band filters according to the present invention, there will be described hereafter certain filters according to the present invention with reference to FIGS. 2, 3, 4 and 5 of the annexed drawings.

DETAILED DESCRIPTION

Figure 1:
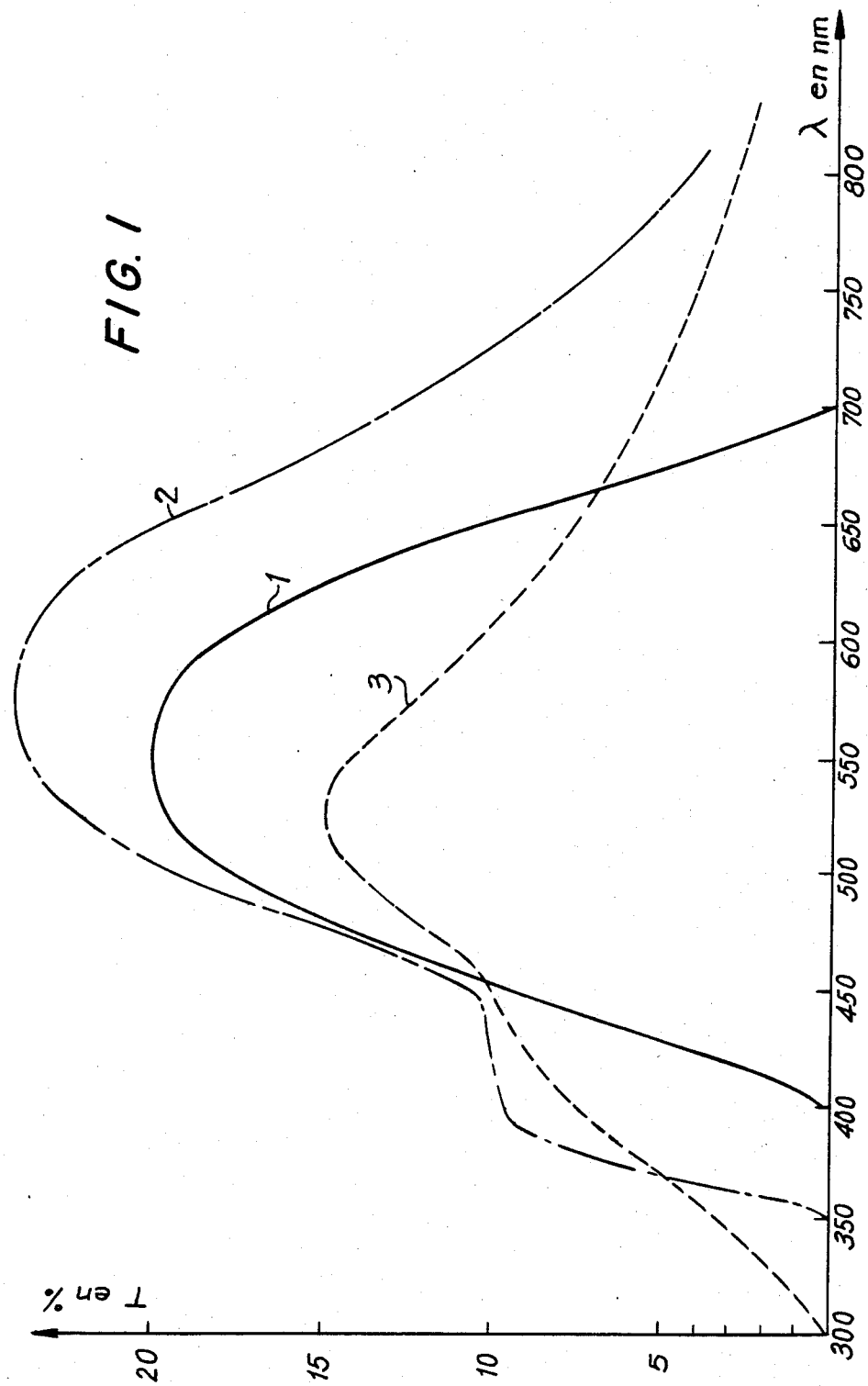
FIG. 1 is a graphical illustration showing the characteristics of an ideal filter and conventional filters.

In the figures, the same numerals will be used to designate layers having the same function. Thus, the metallic layers of the filtering element will always be designated by numerals 22, 24 and 26 whatever the embodiment described in the drawings.

Figure 2:
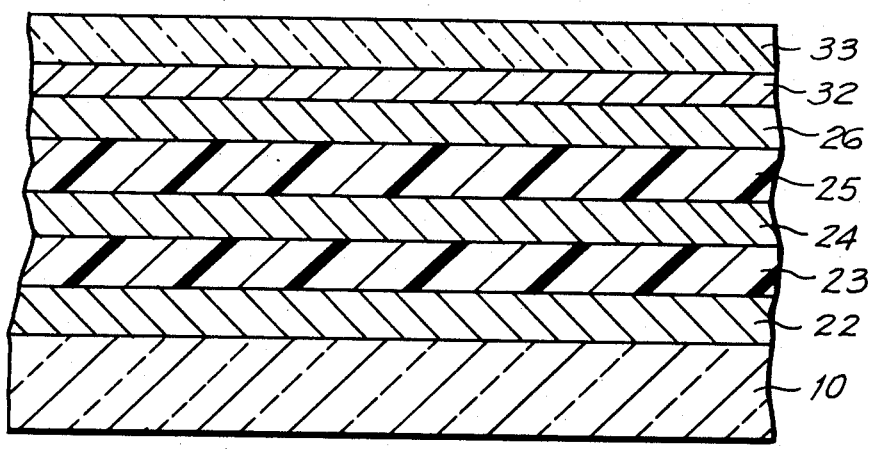
FIG. 2 is a cross-section on enlarged scale of a first embodiment of a filter according to the invention.

FIG. 2 is a transverse section through a band filter in the visable range according to the present invention. This filter is constituted by a support 10 on which is applied a filtering element constituted by three metallic layers 22, 24 and 26 respectively separated by transparent layers 23 and 25. The filtering element is covered with an anti-reflection coating constituted by a metallic layer 32 disposed on the last metallic layer 26 of the filtering element and a transparent layer 33. In this filter, the incident light first meets the support 10.

Figure 3:
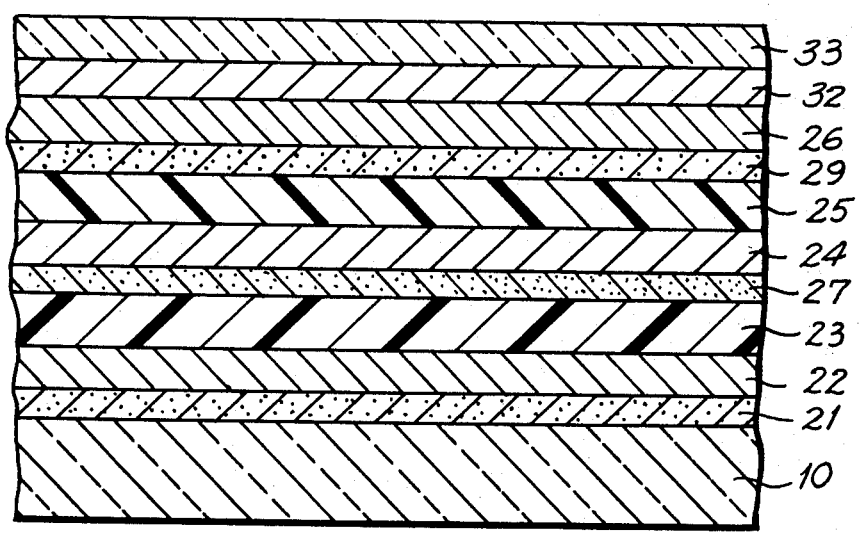
FIGS. 3 – 5 are similar cross-sections of other embodiments.

FIG. 3 is a transverse section of a filter according to the present invention in which there are provided binding and adhering layers. The support 10 is provided with a binding layer 21 in order to improve the adherence of the first metallic layer of the filtering element 22; the transparent layer 23 is disposed directly on the underlying layer 22 without interposition of an adherent layer, assuming the good adherence generally observed in the application of a metallic layer on a transparent layer. In contrast, if necessary adherent layers 27 and 29 can be provided to assure proper connection between the transparent layer 23 and the metallic layer 24 and between the transparent layer 25 and the metallic layer 26. The anti-reflection coating in this embodiment is the same as that described previously with reference to FIG. 2.

Figure 4:
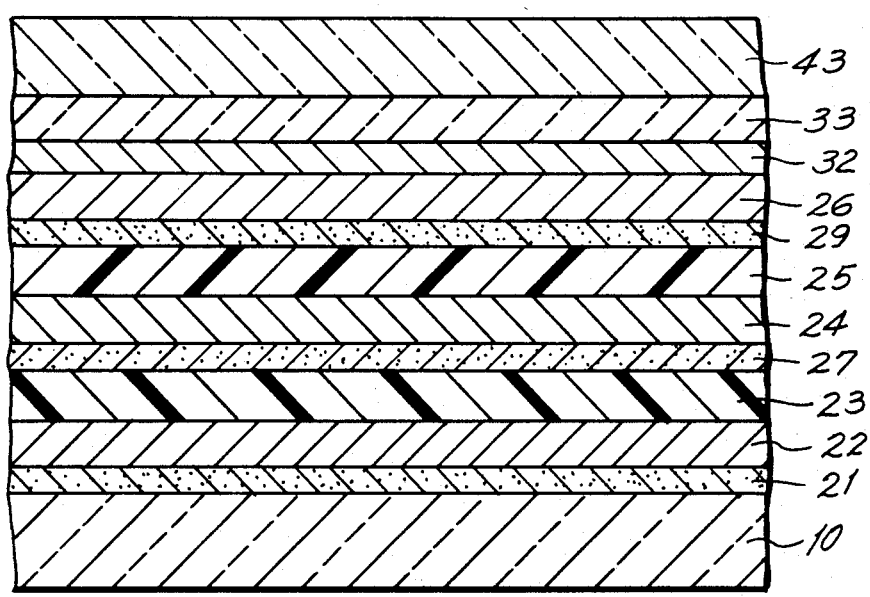

FIG. 4 is a section through the filter of the type of that in FIG. 3 but comprising a protection layer 43 adapted to prevent deterioration of the anti-reflection coating and of the filtering element.

In these two last embodiments, the incident light normally first encounters the support 10.

Figure 5:
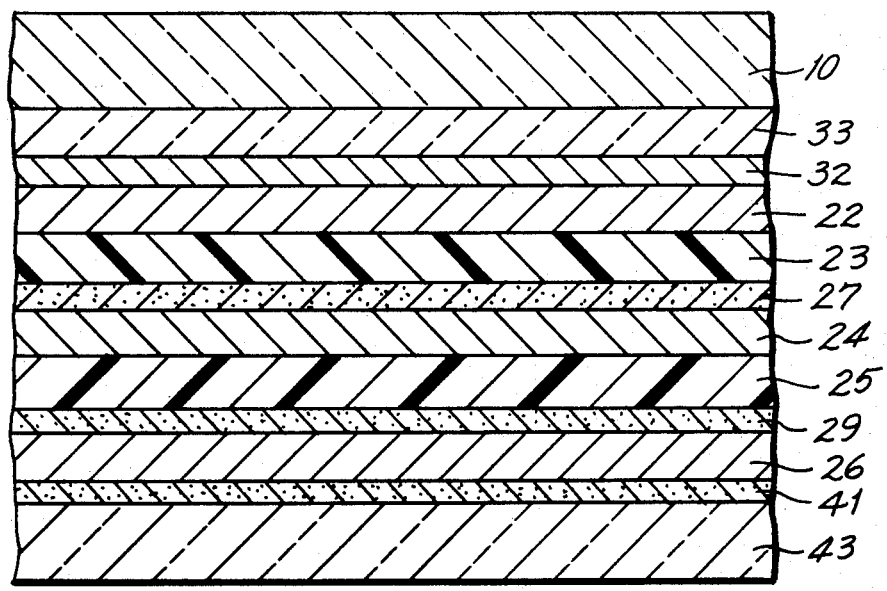

FIG. 5 is a section through a filter according to the present invention in which the difference from the three preceding embodiment is that the incident light first normally encounters the filtering element.

The filter of FIG. 5 comprises the following layers a support 10 on which is applied the anti-reflection coating consisting of transparent layer 33 and metallic layer 32. One of the advantages of this type of stacking is that it is not necessary to provide a binding layer for the first metallic layer 22 on the anti-reflection coating as in the preceding embodiment, the elements utilizable for the formation of the metallic layer of the anti-reflection coating also being utilizable for the binding layer. This is why the metallic layer 22 of the filtering element is directly placed on the metallic layer 32 of the anti-reflection coating. Nevertheless, this advantage is, in general, compensated by the fact that it is necessary as in the present case to provide a protection layer 43 for the filtering element and in order to improve the adherence between this element 43 and the last element 26 of the filtering element, it is necessary to provide a binding layer 41. With regard to the filtering element itself, the stacking is the same as that described in FIG. 4. As has already been stated, in this stacking, the incident light normally first meets the protection layer 43 and the filtering element.

DESCRIPTION OF PREFERRED EMBODIMENTS

The following examples illustrate more precisely the realization of the filters according to the invention without limiting the bounds of the invention.

EXAMPLE 1

A filter as shown in FIG. 4 is produced by vacuum deposition technique in an evaporator of the type BAK 550 made by the Societe Balzers, of Liechtenstein. The supports to be treated (sheets of glass of 50 mm width and of 1mm thickness or curved discs of CR 39 of a diameter of 65 mm) are disposed on a canopy rotating around the axis of the machine whose summit is situated 600 mm from the base thereof. Evaporation devices are situated on an arc of a circle of 200 mm in diameter. At a height of 150 mm from the base of the evaporator are two containers of tungsten and one container of molybdenum. One of these tungsten containers cntains gold or copper metal constituting the optical filtering element, the other contains chromium or an alloy of nickel-chromium which will be utilized to form the intermediary adherence layers and the metallic layer of the anti-reflection coating. In the molybdenum container, there is disposed zinc sulfide which constitutes the transparent layers of the filtering element and of the anti-reflection coating. An apparatus for measuring the thickness of the deposited layers i.e. a quartz scale or an optical system continually measuring the transmission factor or the reflection of the layers (apparatus manufactured by the Societe Balzers, of Liechtenstein) is disposed at the center of the evaporator and in the plane of the canopy. After having effected a vacuum in the evaporator from a pressure of $1 \times 10^{-2}$ Torr to $5 \times 10^{-2}$ Torr, there is produced for 10 m a luminescent discharge adapted to perform a cleaning of the support by ionic bombardment. Then the vacuum is increased to obtain a pressure of $1 \times 10^{-6}$ Torr, and the different layers are deposited without interrupting the vacuum by alternating and successively heating the containers to the evaporation temperature for the products which they contain. When the desired thickness is reached a screen interrupts each layer from evaporation.

Figure 6:
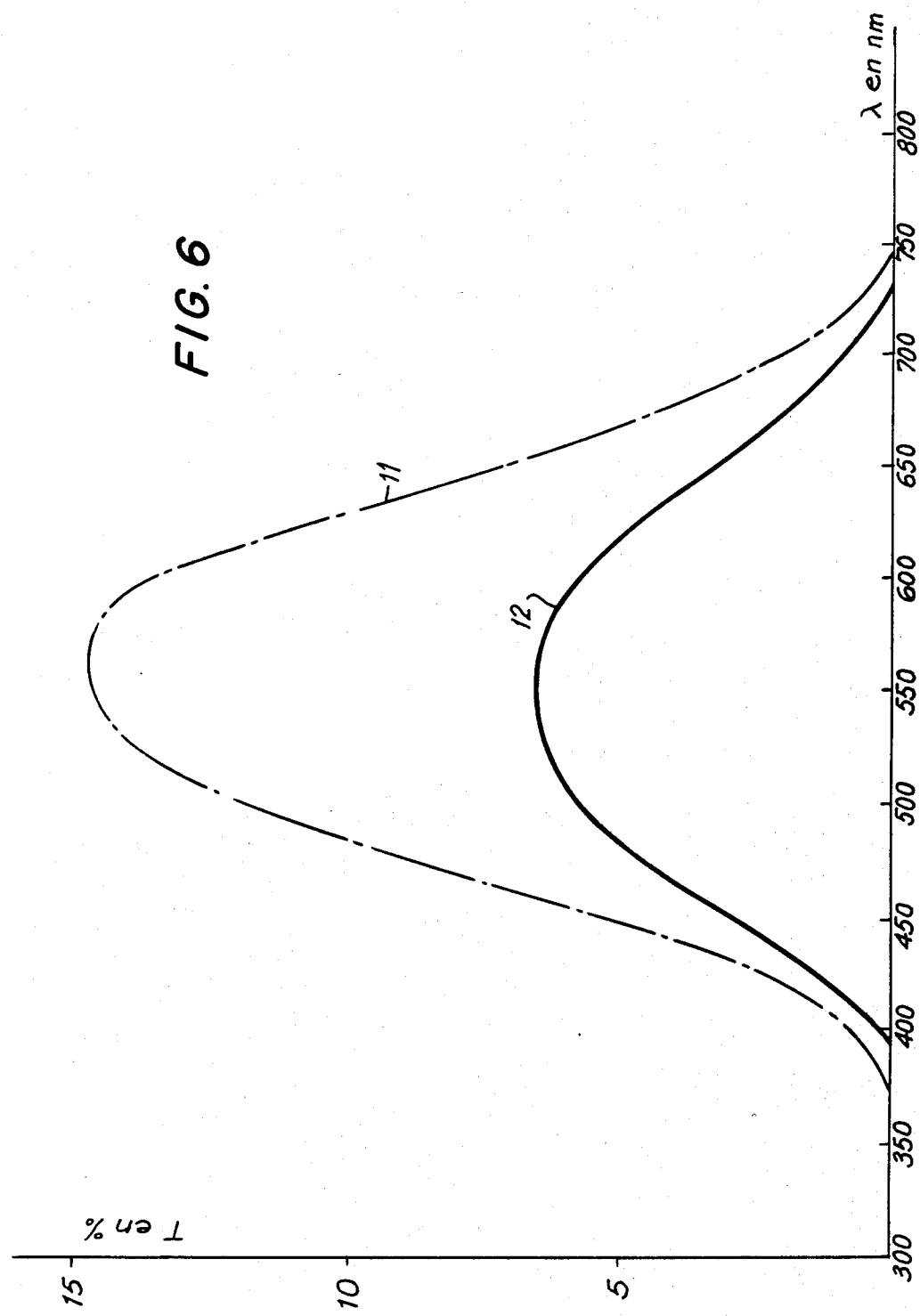
FIG. 6 is a graphical illustration showing the characteristics of filters according to the invention.

The transmission curve 11 of FIG. 6 of the annexed drawings is obtained with a filter of the type of that of FIG. 3 by disposing on the support successively: a layer of chromium of a thickness of 120 nm, a layer of gold of a thickness of 45 nm, a layer of zinc sulfide of a thickness of 60 nm, a layer of chromium of a thickness of 6 nm and a layer of gold of a thicknekss of 45 cm. This stacking constitutes the optical filtering element for ultraviolet and infrared radiation and on this will be applied the anti-reflection coating composed of a layer of chromium of a thickness of 10 nm and a layer of zinc sulfide of a thickness of 40 nm to obtain the complete filter. The atmospheric pressure is then reestablished in the evaporation chamber.

EXAMPLE 2

By operating in a manner analagous to that above, there is obtained the transmission curve 12 of FIG. 6 by successively depositing on the support: a layer of chromium of a thickness of 120 nm, a layer of gold of a thickness of 55 nm, a layer of zinc sulfide of a thickness of 60 nm, a layer of chromium of a thickness of 6 nm, a layer of gold of a thickness of 55 nm, a layer of zinc sulfide of a thickness of 60 nm, a layer of chromium of a thickness of 6 nm, a layer of gold of a thickness of 55 nm, a layer of chromium of a thickness of 10 nm, and a layer of zinc sulfide of a thickness of 40 nm.

If it is desirable to reduce the reflections at the rear face of the filter, there is applied before the deposit of the filtering element onto the support an anti-reflection coating identical to that described hereinabove.

The band filters according to the invention can be partly integrated with sunglasses of current shape or in any optical system whatever adapted to eliminate adverse radiation of the electromagnetic spectrum. They can form the totality of optical systems or represent only one part thereof. The most advantageous embodiments correspond to those shown in FIG. 3 and 4. The filters are then oriented such that the anti-reflection coating will be placed between the transparent support and the eyes of the user.

The present invention therefore concerns the application of band filters described above for the realization of glasses adapted to protect the human eye against infrared and ultraviolet radiation. As a result of experience already realized, in addition to a substantial protection in the visible region such glasses can be realized with much greater tolerances then all glasses of the same type known to the present and which constitutes a considerable advantage from the industrial and commercial point of view.

What is claimed is:

1. A band filter adapted to allow passage only of a band length between 350 and 750 nm, said filter consisting essentially of a support which is at least partially transparent in the considered band, a filter element coated on at least one of the two faces of said support, said filter element consisting of three metallic layers respectively separated by two layers of transparent material, said layers of transparent material having an index of refraction greater than 1.5, the optical thickness of the layers of transparent material each being equal to about ¼ of the mean wave length of the considered band, one of said metallic layers of said filter elements having a surface within about 15 nm of said support, and an anti-reflection coating on the outer surface of said filter element opposite said support, said anti-reflection coating consisting of a layer of a metallic or semi-metallic element on the other of said outer metal layers of said outer surface and a layer of transparent material disposed on said layer of metallic or semi-metallic element.

2. A band filter as claimed in claim 1 wherein the metallic layers of the filter element are selected from the group consisting of aluminum, silver, rhodium, platinum, copper and gold.

3. A band filter as claimed in claim 1 wherein the metallic layers of the filter element are gold.

4. A band filter as claimed in claim 1 wherein the transparent material is selected from the group consisting of bismuth oxide, lead oxide, tin oxide, indium oxide, titanium dioxide, zirconium oxide, niobium oxide, tantulum pentoxide, aluminum oxides, silicon oxides and zinc sulfide.

5. A band filter as claimed in claim 1 wherein the transparent material is titanium oxide or zinc sulfide.

6. A band filter as claimed in claim 1 comprising a binding layer between the support and the contiguous metallic layer of the filter element and an adherence layer between at least one transparent layer and the contiguous metallic layer, said binding and adherence layers being a metallic or semi-metallic element.

7. A band filter as claimed in claim 6 wherein said metallic or semi-metallic element of the anti-reflection coating and metallic or semi-metallic element of the binding and adherence layers is selected from the group consisting of iron, titanium, tungsten, nickel, tantalum, molybdenum, niobium, zinc, cadmium, vanadium, tin, indium, lanthanum, lead, aluminum, zirconium, iridium, yttrium, hafnium, rhenium, cobalt, thallium, chromium, alloys of nickel chromium, germanium, silicon, antimony, tellurium and arsenic.

8. A band filter as claimed in claim 1 wherein the thickness of the metallic elements of the filter element is between about 40 and 60 nm.

9. A band filter as claimed in claim 1 wherein the transparent layer of the anti-reflection coating has a thickness between about 35 and 45 nm, and the layer of the metallic or semi-metallic material of the anti-reflection coating has a thickness between about 5 and 20 nm.

10. A band filter as claimed in claim 6 wherein the binding layer has a thickness between 10 and 15 nm and the adherence layer has a thickness between 5 and 7 nm.

11. A band filter as claimed in claim 6 wherein the metallic layers of the filter element are gold, the transparent layers are zinc sulfide and the binding and adherence layers are chromium.

12. A filter as claimed in claim 1 for glasses for the protection of the human eye.

* * * * *